United States Patent
Ankersen et al.

[11] Patent Number: 6,083,960
[45] Date of Patent: Jul. 4, 2000

[54] CONSTRAINED SOMATOSTATIN AGONISTS AND ANTAGONISTS

[75] Inventors: Michael Ankersen, Frederiksberg; Florenzio Zaragoza Dorwald, Herlev; Carsten Enggaard Stidsen, Soborg, all of Denmark; Albert Michael Crider, Monroe, La.

[73] Assignee: Novo Nordisk A/S, Bagsvaerd, Denmark

[21] Appl. No.: 09/397,355

[22] Filed: Sep. 16, 1999

Related U.S. Application Data

[62] Division of application No. 08/962,098, Oct. 31, 1997, Pat. No. 6,020,349.

[30] Foreign Application Priority Data

Oct. 31, 1996 [DK] Denmark .................. 1216/96

[51] Int. Cl.[7] .................. A61K 31/445; C07D 295/194
[52] U.S. Cl. .................. 514/318; 514/255; 514/338; 514/344; 514/866; 544/360; 544/364; 546/193; 546/194; 546/268.4; 546/274.1
[58] Field of Search ................ 546/193, 194, 546/268.4, 274.1; 544/360, 364; 514/255, 318, 338, 341, 866

[56] References Cited

U.S. PATENT DOCUMENTS 4,203,988  5/1980  Bolhofer et al. .................. 424/266
5,021,431  6/1991  Buschauer et al. .................. 514/333

FOREIGN PATENT DOCUMENTS

| 0 304 330 A1 | 2/1989 | European Pat. Off. . |
| 0 448 765 A1 | 10/1991 | European Pat. Off. . |
| 3631 334 Al | 3/1988 | Germany . |
| WO 87/07891 | 12/1987 | WIPO . |

OTHER PUBLICATIONS

Woderer et al., Chem. Ber. 119, 2050–2054, (1986).

*Primary Examiner*—Shailendra Kumar
*Attorney, Agent, or Firm*—Steve T. Zelson, Esq.; Elias J. Lambiris, Esq.

[57] ABSTRACT

The present invention relates to a compound of general formula I

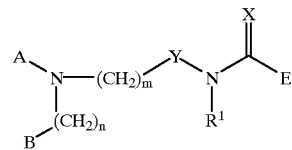

for treating medical disorders related to binding to human somatostatin receptor subtypes.

11 Claims, No Drawings

CONSTRAINED SOMATOSTATIN AGONISTS AND ANTAGONISTS

CROSS-REFERENCE TO RELATED APPLICATIONS

This application is a Divisional application of Ser. No. 08/962,098 filed Oct. 31, 1997 now U.S. Pat. No. 6,020,349.

FIELD OF INVENTION

The present invention relates to compounds, pharmaceutical compositions containing them, methods of treatment and their use for preparing pharmaceutical compositions for treating medical disorders related to binding to human somatostatin receptor subtypes.

BACKGROUND OF THE INVENTION

Somatostatin (somatotropin release inhibiting factor; SRIF), a tetradecapeptide originally isolated from ovine hypothalamus on the basis of its ability to inhibit growth hormone release from anterior pituitary cells (Brazeau, P. et al., Science 179, 77–79, 1973) has been shown to be present in several other tissues (for a review see Reichlin, S., N. Engl. J. Med. 309, 1495–1501, 1983 and ibid, 1556–1563). Somatostatin appears to have widespread functions as a modulator of neuronal activity as well as of endocrine and exocrine secretion. Inhibitory effects of this peptide on the release of a variety of hormones such as growth hormone, prolactin, glucagon, insulin, gastrin and thyroid stimulating hormones have been described (for a review see Wass, J. A. H., in Endocrinology, ed. deGrott, L. J., vol 1, 152–166, 1989). Somatostatin is best regarded as belonging to a phylogenetically ancient, multigene family of peptides with two important bioactive products, namely SRIF-14 (SRIF) and SRIF-28, a congener of SRIF extended at the N-terminus.

The regulatory functions of SRIF are mediated by specific membrane receptors. Currently, only agonists are available to study the pharmacology of SRIF receptors. High-affinity saturable binding sites have been demonstrated in a number of tissues, e.g. pituitary gland, brain and pancreas. Within the last few years the cloning and isolation of five somatostatin receptor genes has been reported for various species (human, rat, mouse and bovine). Structural analysis of the encoded proteins revealed that the somatostatin receptor proteins (SST1–SST5) represent a distinct receptor subfamily (named the A5 subfamily) belonging to the superfamily of G protein-coupled receptors with seven putative membrane spanning regions.

Recent work on the development of nonpeptide structures substituting the peptide backbone of small cyclic peptides with a β-D-glucose scaffold (Hirschmann, R. et al, J.Am. Chem.Soc. 115, 12550–12568, 1993) or xylofuranose scaffold (Papageorgiou, C. et al., Bioorg.Med.Chem.Lett. 2, 135–140, 1992) demonstrated low somatostatin receptor affinity. However, these structures are nonselective displaying higher affinities for both β2-adrenergic receptors and tachykinin receptors. Thus, there have been no reports in the literature on the successful development of a selective, competitive somatostatin receptor ligand of nonpeptide origin.

The H3 receptor is known and of current interest for the development of new medicaments (see. e.g. Stark, H.; Schlicker, E.; Schunack, W. Drugs Fut. 1996, 21, 507–520; Leurs, R.; Timmerman, H.; Vollinga, R. C. Progress in Drug Research 1995, 45, 107–165). The histamine H3 receptor is a presynaptic autoreceptor located in both the central and the peripheral nervous system, the skin and in organs such as the lung, the intestine, probably the spleen and the gastrointestinal tract. Stimulation of the H3 receptor with an agonist leads to an inhibition of the biosynthesis and the release of histamine (autoreceptor), and also of other neurotransmitters (heteroreceptor), such as serotonine and acetylcholine. These findings indicate that the H3 receptor is a target for new therapeutics.

SUMMARY OF THE INVENTION

Accordingly, the present invention relates to a compound of general formula I

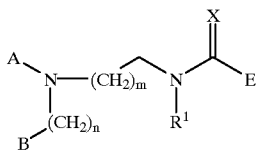

formula I wherein

A is aryl, optionally substituted with one or more halogens, amino groups, hydroxyl groups, nitro groups, $C_{1-6}$-alkyl groups, $C_{1-6}$-alkoxy groups or aryl groups, B is aryl, optionally substituted with one or more halogens, amino groups, hydroxyl groups, $C_{1-6}$-alkyl groups, $C_{1-6}$-alkoxy groups or aryl groups, m is 0, 1, 2, 3, 4, 5 or 6, n is 0, 1, 2 or 3, Y is a valence bond or a group having the formula

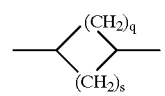

wherein q and s each independently are 0, 1, 2, 3, 4 or 5, and q+s is 1, 2, 3, 4 or 5, $R^1$ is hydrogen or $C_{1-6}$-alkyl optionally substituted with halogen, amino, hydroxy, alkoxy or aryl;

X is =S, =O or =$NR^3$, wherein $R^3$ is hydrogen, —C(O)Ph, or —CN,

E is a group having the formula

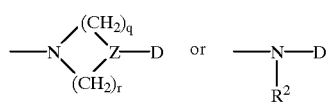

wherein p is 0, 1, 2, 3 or 4, r is 1, 2, 3, 4, 5 or 6,

Z is —N< or —CH<,

D is aryl, optionally substituted with one or more halogens, amino groups, hydroxyl groups, $C_{1-6}$-alkyl groups, $C_{1-6}$-alkoxy groups, piperidinyl groups or aryl groups;

$R^2$ is hydrogen or $C_{1-6}$-alkyl optionally substituted with halogen, amino, hydroxy, alkoxy or aryl, with the proviso that if m=0 then Y is not a valence bond; and the pharmaceutically acceptable salts thereof.

The compounds of formula I comprise any optical isomers thereof, in the form of separated, pure or partially purified optical isomers or racemic mixtures thereof.

DETAILED DESCRIPTION OF THE INVENTION

In the above structural formulas and throughout the present specification, the following terms have the indicated meanings:

The $C_{1-6}$-alkyl groups specified above are intended to include those alkyl groups of the designated length in either a linear or branched or cyclic configuration. Examples of linear alkyl are methyl, ethyl, propyl, butyl, pentyl, and hexyl. Examples of branched alkyl are isopropyl, sec-butyl, tert-butyl, isopentyl, and isohexyl. Examples of cyclic alkyl are $C_{3-6}$-cycloalkyl such as cyclopropyl, cyclobutyl, cyclopentyl and cyclohexyl.

The alkoxy groups, preferably $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are $C_{3-6}$-cycloalkoxy such as cyclopropyloxy, cyclobutyloxy, cyclopentyloxy and cyclohexyloxy.

In the present context, the term "aryl" is intended to include aromatic rings, such as carbocyclic and heterocyclic aromatic rings selected from the group consisting of phenyl, naphthyl, thienyl, furyl, furanyl, pyridinyl, pyridyl, 1-H-tetrazol-5-yl, thiazolyl, imidazolyl, isoquinolinyl, indolyl, isoindolyl, piperazinyl, pyridazinyl, pyrimidinyl, thiadiazolyl, pyrazolyl, oxadiazol, oxazolyl, isoxazolyl, thiophenyl, quinolinyl, pyrazinyl, triazinyl, triazolyl, tetrazolyl, isoindazolyl, benzotriazolyl or isothiazolyl, optionally substituted by one or more halogen, amino, hydroxy, carboxylic acid, carboxylic amide, nitrile, aldehyde, nitro, trihalogenomethyl, $C_{1-6}$-alkylketone, $C_{1-6}$-alkyl, $C_{1-6}$-alkoxy or aryl.

The term "$C_{1-6}$-alkylketone" is intended to include the above $C_{1-6}$-alkyl groups connected to a ketone group.

The term "halogen" is intended to include Cl, F, Br and I.

The term "treatment" is intended to comprise treatment of a patient, such as a mammal, e.g. a human, having a disease as well as profylactic treatment of said patient in order to inhibit or control the disease.

In a preferred embodiment of the above compound of formula I $R^1$ and $R^2$ are each independently hydrogen or $C_{1-6}$-alkyl, such as hydrogen.

In another preferred embodiment of the above compound of formula I $(CH_2)_r$ is a $C_{1-6}$ alkylene, such as methylene, ethylene, propylene, butylene, pentylene and hexylene, e.g. methylene, ethylene or propylene, such as ethylene.

In a further preferred embodiment of the above compound of formula I Y is a valence bond or q and s are each independently 0, 1, 2, 3 or 4 and q+s is 3 or 4.

In a still further preferred embodiment of the above compound of formula I X is =S, =NH or =NC(O)Ph. In a particular embodiment X is =S.

In a further preferred embodiment of the above compound of formula I A is phenyl or pyridinyl, optionally substituted with one or two halogens, amino groups, hydroxyl groups, nitro groups, $C_{1-6}$-alkyl groups, $C_{1-6}$-alkoxy groups or aryl groups, such as pyridinyl optionally substituted with one halogen, such as bromine.

In a still further preferred embodiment of the above compound of formula I B is phenyl or pyridinyl, optionally substituted with one or two halogens, amino groups, hydroxyl groups, $C_{1-6}$-alkyl groups, $C_{1-6}$-alkoxy groups or aryl groups, such as phenyl optionally substituted with one or two halogens, such as chlorine and/or bromine.

In a further preferred embodiment of the above compound of formula I D is phenyl, benzotriazolyl, imidazolyl or pyridinyl, optionally substituted with one or two halogens, amino groups, hydroxyl groups, $C_{1-6}$-alkyl groups, $C_{1-6}$-alkoxy groups, piperidinyl groups or aryl groups, such as optionally substituted with one piperidinyl or imidazolyl. In a particular embodiment D is phenyl substituted with an imidazolyl group or is imidazolyl, optionally substituted with one or two halogens, amino groups, hydroxyl groups, $C_{1-6}$-alkyl groups, $C_{1-6}$-alkoxy groups, piperidinyl groups or aryl groups.

In a still further preferred embodiment of the above compound of formula I m is 0, 1, 2, 3 or 4, such as 2, 3 or 4.

In a further preferred embodiment of the above compound of formula I n is 0, 1 or 2, such as 1.

In a still further preferred embodiment of the above compound of formula I p is 0, 1 or 2, such as 0 or 2.

In a further preferred embodiment of the above compound of formula I r is 1, 2 or 3, such as 2.

In a still further preferred embodiment of the above compound of formula I q+s is 2, 3 or 4, such as 3 or 4.

Whenever a heteroaryl or aryl is substituted such substitution(s) may be in any possible ring position, which may be recognized by the skilled person without any undue burden.

In a broader aspect the invention relates to somatostatin receptor ligands of nonpeptide origin, including the compounds of formula I, which have affinity to the somatostatin receptor proteins selected from SST1, SST2, SST3, SST4 and SST5.

In an embodiment of the somatostatin receptor ligands of nonpeptide origin, said ligands have selective affinity to one or two of the somatostatin receptor proteins selected from SST1, SST2, SST3, SST4 and SST5.

In a further embodiment of the somatostatin receptor ligands of nonpeptide origin, said ligands have selective affinity to SST1.

In a still further embodiment of the somatostatin receptor ligands of nonpeptide origin, said ligands have selective affinity to SST2.

In a further embodiment of the somatostatin receptor ligands of nonpeptide origin, said ligands have selective affinity to SST3.

In a still further embodiment of the somatostatin receptor ligands of nonpeptide origin, said ligands have selective affinity to SST4.

In a further embodiment of the somatostatin receptor ligands of nonpeptide origin, said ligands have selective affinity to SST5.

In a still further embodiment of the somatostatin receptor ligands of nonpeptide origin, said ligands have selective affinity to SST1 and SST2, SST2 and SST3, SST3 and SST4, SST4 and SST5, SST1 and SST3, SST2 and SST4 or SST3 and SST5.

Preferred compounds of the present invention are 1-(2-((5-Bromopyridin-2-yl)-(3,4-dichlorobenzyl)amino) ethyl)-3-(4-piperidine-1-ylphenyl)thiourea

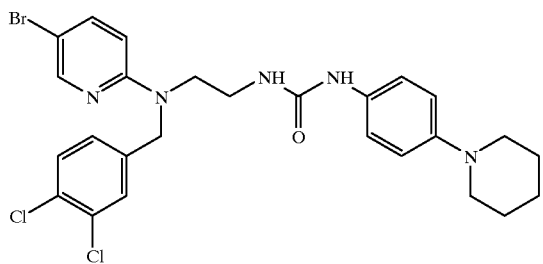

1-(3H-Benzotriazol-5-yl)-3-(2-((5-bromopyridin-2-yl)-
(3,4-dichlorobenzyl)amino)ethyl)thiourea

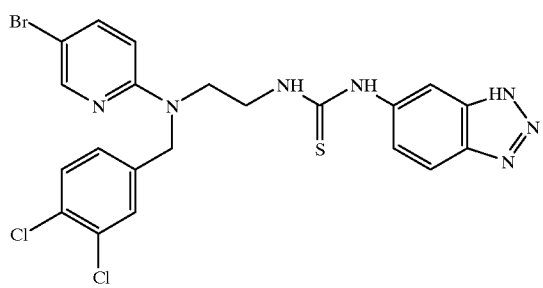

4-(1H-Imidazol-4-yl)piperidine-1-carbothioic acid (2-((5-
bromopyridine-2-yl)-(3,4-dichlorobenzyl)amino)ethyl)
amide

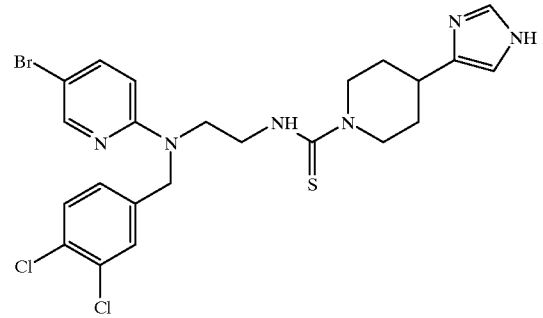

1-(2-((5-Bromopyridin-2-yl)-(3,4-dichlorobenzyl)amino)
propyl)-3-(4-piperidine-1-ylphenyl)thiourea

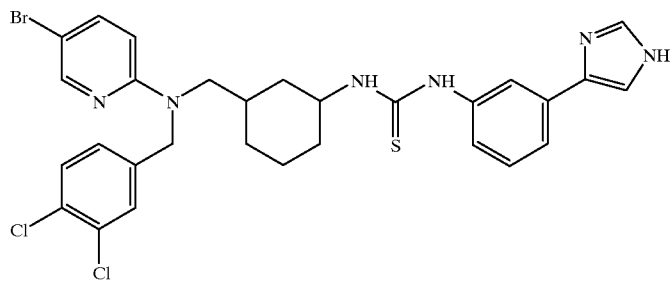

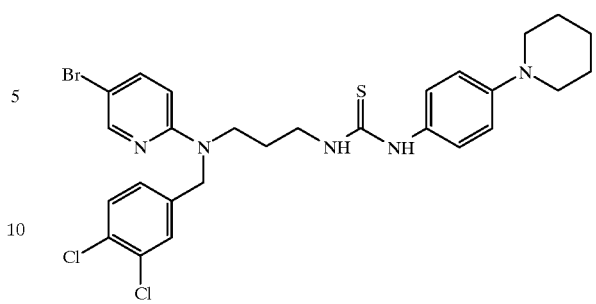

1-(2-((5-Bromopyridin-2-yl)-(3,4-dichlorobenzyl)amino)
butyl)-3-(3-(1H-imidazol-4-yl)phenyl)thiourea

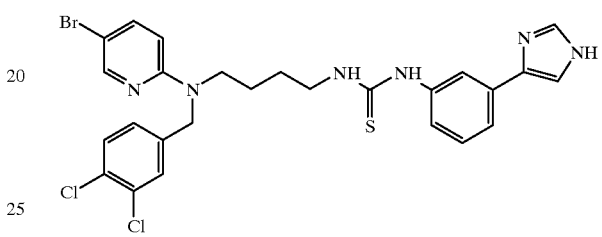

$N^1$-(3-(N-(4-Bromobenzyl)-N-(pyridin-2-yl)amino)
propyl)-4-(pyridine-2-yl)piperazine-1-carboxamidine

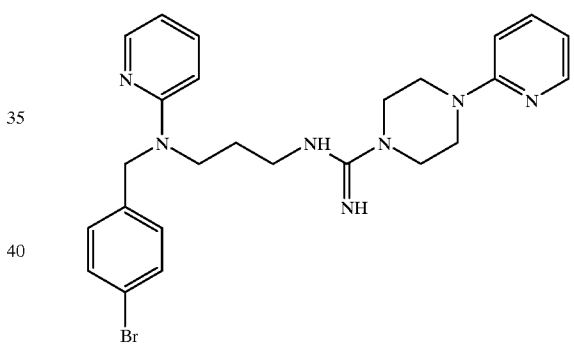

1-(3-(((5-Bromopyridin-2-yl)-(3,4-dichlorobenzyl)
amino)methyl)cyclohexyl)-3-(3-(1H-imidazol-4-yl)
phenyl)thiourea $N^1$-(3-(N-(4-Bromobenzyl)-N-(pyridin-2-yl)amino)
cyclopentyl)-4-(pyridin-2-yl)piperazine-1-
carboxamidine

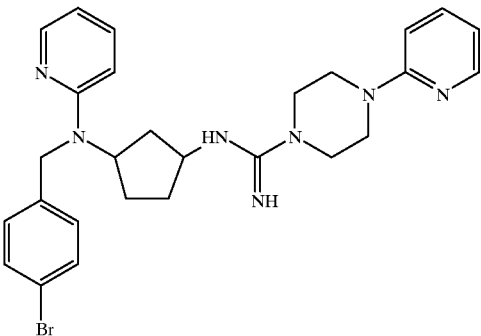

The compounds of the invention can be employed to mediate the biological effects of somatostatin agonists or antagonists. It is believed that compounds of formula I exhibit an improved bioavailability because they contain no amide bonds susceptible to cleavage by proteolytic enzymes. The increased resistance to proteolytic degradation combined with the reduced size of the compounds of the invention in comparison with known somatostatin agonists and antagonists is expected to possess beneficial properties such as increased peroral absorption, increased biological half-life, lack of immunogenicity, and the ability to cross the blood-brain barrier compared to that of the compounds suggested in the prior literature.

Compounds of formula I are believed to be useful for the development of pharmaceutical, therapeutic, and diagnostic techniques. Accordingly, the invention also provides methods for producing a prophylactic or therapeutic response in a mammal by administering to the mammal a pharmaceutically effective amount of one or more compounds of the invention. In accordance with preferred embodiments, the present invention provides methods for producing such responses by modulating the activity of mammalian somatostatin receptors by administering an effective amount of one or more compounds of the invention.

In another aspect of the present invention the compounds of formula I wherein D is phenyl substituted with imidazolyl or is imidazolyl, optionally substituted with one or more halogens, amino groups, hydroxyl groups, $C_{1-6}$-alkyl groups, $C_{1-6}$-alkoxy groups, piperidinyl groups or aryl groups, interact with the H3 receptor and may thus be used for the treatment of airway disorders such as asthma, as anti-diarrhoeals and for the modulation of gastric acid secretion. The compounds of the present invention may also be used for the treatment of diseases associated with the regulation of sleep and wakefulness and for the treatment of narcolepsy and attention deficite disorders. Moreover these new compounds may be used as non-amphetamine-like stimulants or as sedatives. Further, the compounds of the invention may be used for the treatment of eating disorders (e.g. anorexia or bulimia) by virtue of their appetite regulating properties. Thus, these compounds may be useful for the prevention of diseases related to obesity, such as diabetes and cardiovascular disorders. The present compounds could also be used for treatment of conditions associated with epilepsy. Additionally these compounds can be used for the treatment of motion sickness and vertigo. Further, the compounds of the present invention may be used for the treatment of dementia and Alzheimer disease.

The compounds of the present invention may have one or more asymmetric centers and stereoisomers in the form of separated, pure or partially purified stereoisomers or racemic mixtures thereof are intended to be included in the scope of the invention.

GENERAL METHODS

General Method A
Reaction Scheme I:

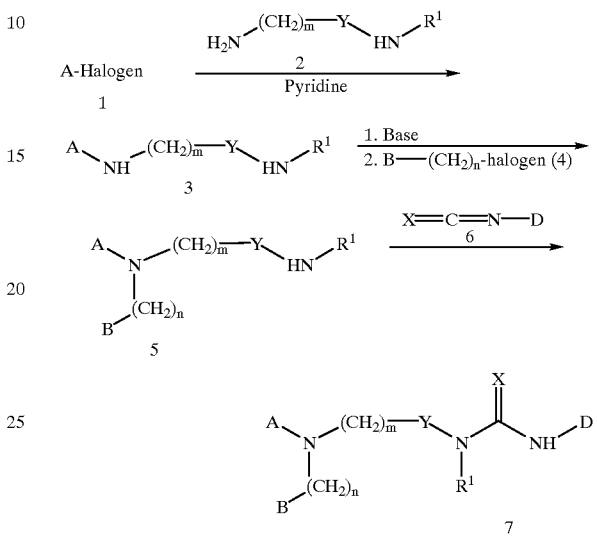

Compounds of formula I may be prepared as shown in reaction scheme I starting with an arylhalogenide 1 which may be reacted with a diaminoalkyl 2 in an appropriate solvent such as pyridine and under nitrogen at reflux for an appropriate time. The excess diaminoalkyl and solvent may be removed in vacuo and an apolar solvent such as tetrahydrofuran may be added to precipitate the diaminoalkyl salt. The intermediate 3 may be obtained by distillation or chromatography by methods known in the art.

The intermediate 3 may be alkylated with an arylalkylhalogenide 4 after treatment with a base such as sodium hydride under conditions known in the art to give a 1,1-disubstituted primary or secondary amine 5. Then 5 in a solvent like tetrahydrofuran or ethanol may be reacted with an isothiocyanate (or isocyanate) 6, prepared as shown in scheme 2 or by methods known for those skilled in the art, stirred overnight and concentrated in vacuo to afford a crude product 7. The isothiocyanate (or isocyanate) may be protected and deprotected according to methods described in the art (e.g. T. W. Greene, Protective Groups in Organic Synthesis, 2nd. edition, John Wiley and Sons, New York, 1991). The crude product 7 may be purified by methods known for those skilled in the art such as chromatography, to yield the final product 7 which is a compound of the general formula I.

Reaction Scheme II:

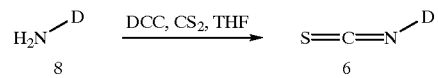

The isothiocyanate 6 as described in scheme I may be prepared from the appropriate protected primary amine 8 in a solvent like tetrahydrofuran and carbondisulfide in the presence of a reagent such as dicyclohexylcarbodiimide or other coupling reagents known in the literature under chilled conditions. The mixture may be stirred overnight and the solvent removed and the residue may be triturated with ether to remove dicyclohexylthiourea. The remaining product may be distilled under vacuum or chromatographed using technics known to those skilled in the art, to yield the isothiocyanate 6.

The corresponding isocyanate 6b may be prepared from a protected primary amine 8 and carbonyldiimidazole in an appropriate solvent following procedures known for those skilled in the art.

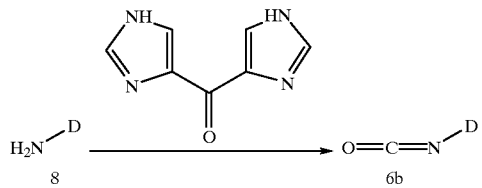

General Method B
Reaction Scheme III

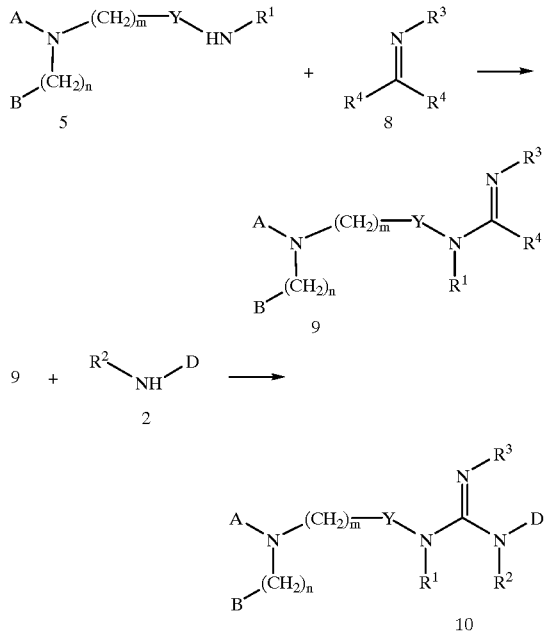

Compounds of formula I may be prepared as shown in reaction scheme III starting with an appropriate amine 5, prepared as described in reaction scheme I, and an activated imine 8 in which $R^3$ may be benzoyl (—COPh) or nitrile (—CN) and $R^4$ may be thiomethoxy (—SCH$_3$), phenoxy (—OPh) or chloride (—Cl) in an appropriate solvent such as dimethylformamide or tetrahydrofuran at an appropriate temperature for an appropriate time to give the intermediate 9. The intermediate 9 may further react with an amine 2 in an appropriate solvent such as pyridine with or without a catalyst e.g. silver salts (e.g. AgNO$_3$) at an appropriate temperature for an appropriate time to form the product 10 which is a compound of the general formula I.

When the compound 10 (in which $R^3$ is an activating group such as benzoyl or nitrile) is treated with 1.5 M aqueous hydrogen chloride for an appropriate time at an appropriate temperature the compound 10 (in which $R^3$ is hydrogen) may be formed which is a compound of the general formula I.

The intermediates in reaction scheme III may be protected and deprotected according to methods described in the art (e.g. T. W. Greene, Protective Groups in Organic Synthesis, 2nd. edition, John Wiley and Sons, New York, 1991).

The guanidine derivatives and their salts thus obtained can be isolated and purified by methods which are known by those skilled in the art.

General Method C
Reaction Scheme IV:

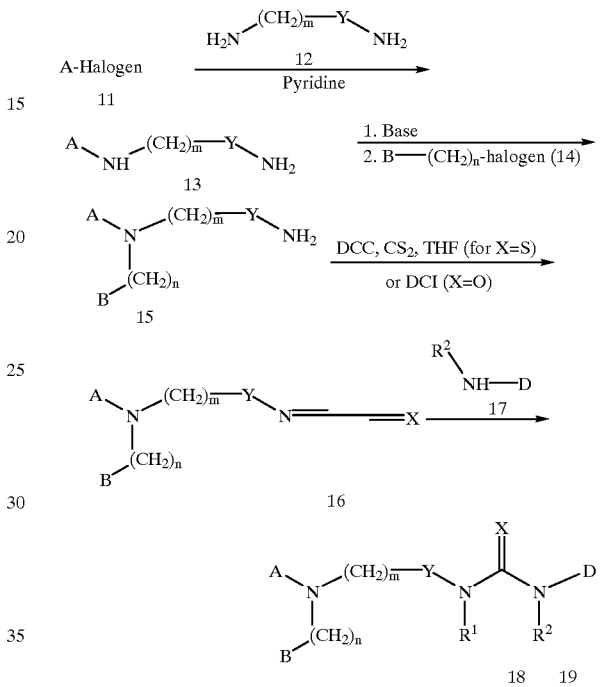

Compounds of formula I may be prepared as shown in reaction scheme I starting with an arylhalogenide 11 which may be reacted with a diaminoalkyl 12 in an appropriate solvent such as pyridine and under nitrogen at reflux for an appropriate time. The excess diaminoalkyl and solvent may be removed in vacuo and an apolar solvent such as tetrahydrofuran may be added to precipitate the diaminoalkyl salt. The intermediate 13 may be obtained by distillation or chromatography by methods known in the art.

The intermediate 13 may be alkylated with an arylalkylhalogenide 14 after treatment with a base such as sodium hydride under conditions known in the art to give a 1,1-disubstituted primary amine 15.

The isothiocyanate (X═S) or isocyanate (X═O) 16 may be obtained by methods as described in scheme II or by methods known for those skilled in the art.

Then 16 in a solvent like tetrahydrofuran or ethanol may be reacted with an amine 17, stirred overnight and concentrated in vacuo to the thiourea or urea 18. The thiourea or urea may be protected and deprotected according to methods described in the art (e.g. T. W. Greene, Protective Groups in Organic Synthesis, 2nd. edition, John Wiley and Sons, New York, 1991). The crude product 18 may be purified by methods known for those skilled in the art such as chromatography, to yield the final product which is a compound of the general formula I.

Pharmacology

Compounds of the invention are preferred to the extent that they selectively and effectively are bound by somatostatin receptor subtypes permanently expressed in eukaryotic cell lines. It will be recognized that the degree to which a compound is bound by a receptor is known as its binding affinity. The affinity of a compound is commonly expressed as the inhibitory concentration at which the compound is able to displace 50% of another compound already bound to the receptor ($IC_{50}$). In the case of ligand-binding studies at somatostatin receptors, the compound that is displaced is a radioactive agonist, e.g. $^{125}I$-$Tyr^{11}$-SRIF-14, at the receptor. It is preferred in accordance with the present invention that a compound possess a clinically effective $IC_{50}$ in at least one mammal; that is, it should possess an $IC_{50}$ which is low enough to inhibit binding of radiolabelled agonist to somatostatin receptors while causing a minimum of unacceptable side effects in the mammal. As will be recognized, clinically effective concentrations vary depending on a number of factors, such as the pharmacokinetic characteristics and stability of the compound under study and thus must be determined empirically for each compound and each factor. In general, it is desired that the potency of a compound of the invention be as great as possible, preferable greater than or equal to the native somatostatin. Compounds displacing radiolabelled agonist at somatostatin receptors could belong to one of two classes, either agonists or antagonists. Simple ligand-binding studies will not distinguish between these two classes. All five somatostatin receptor subtypes have been shown to inhibit the activity of adenylyl cyclase via the G protein subunit $G_i$ (Patel, Y. C. et al. Biochem. Biophys.Res.Commun., 198:605–612, 1994). By direct activation of adenylyl cyclase by forskolin the inhibitory action of somatostatin agonists could be employed. Compounds specifically reversing the inhibitory action of SRIF on cyclic AMP accumulation will be termed somatostatin receptor antagonists.

Those skilled in the art will appreciate that a wide variety of prophylactic, diagnostic, and therapeutic treatments may be prepared from the compounds and compositions of this invention, due to agonism or antagonism at somatostatin receptors. For example, by administering an effective amount of compound, prophylactic or therapeutic responses can be produced in a human or some other type mammal. Preferred responses are modulation of glucagon and insulin secretion to treat type I and type II diabetes; inhibition of cell proliferation and growth to treat various endocrine and exocrine tumors; modulation of growth hormone secretion to treat dwarfism, acromegaly, and other growth abnormalities; modulation of immune responses to treat autoimmune diseases, rheumatoid arthritis, and other inflammations; modulation of neuronal activity to treat diseases related to the central nervous system, i.e. pain, anxiety, memory disorders, affective disorders, and Alzheimer's disease; modulation of intestinal water uptake to treat congestion and diarrhea; inhibition of arterial smooth muscle cell proliferation to treat restenosis and arteriosclerosis; inhibition of airway mucous secretion to treat asthma and mucoviscidosis; modulation of lipid metabolism and regulation of energy balance to treat obesity; inhibition of acid secretion to treat ulcer; inhibition of pancreatic secretions to treat acute pancreatitis; and treatment of chronic fatigue syndrom (CFS). It will be appreciated that the production of prophylactic or therapeutic responses includes the initiation or enhancement of desirable responses, as well as the cessation or suppression of undesirable responses. When, in particular a compound of the invention, or a pharmaceutically acceptable salt thereof, has high and/or selective affinity to the somatostatin receptor protein designated SSTR4, such compound may be useful for the treatment of a disease associated with an adverse condition in the retina and/or iris-ciliary body of a mammal. Such conditions being high intraocular pressure (IOP) and/or deep ocular infections. The diseases which may be treated are e.g. glaucoma, stromal keratitis, iritis, retinitis, cataract and conjunctivitis.

As can be seen, the present invention provides a variety of compounds which effectively and selectively are bound to somatostatin receptors. The compounds are capable of forming pharmaceutically acceptable salts with various inorganic and organic acids, and such salts are also within the scope of this invention. Examples of such salts are acid addition salts including acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts may be formed by conventional means, such as by reacting the free base form of the product with one or more equivalents of the appropriate acid in a solvent or medium in which the salt is insoluble, or in a solvent such as water, which is later removed in vacuo or by freeze drying. The salts also may be formed by exchanging the anions of an existing salt for another anion on a suitable ion exchange resin.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |

-continued

| | |
|---|---|
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 1–500 mg/day, e.g. about 100 mg per dose, when administered to patients, e.g. humans, as a drug.

It has been demonstrated that compounds of the general formula I possess the ability to bind to human somatostatin receptors. The compounds may therefor be used in the treatment of conditions which require high somatostatin receptor affinity.

Thus, in a particular aspect, the present invention relates to a pharmaceutical composition for binding to somatostatin receptors, the composition comprising, as an active ingredient, a compound of the general formula I or a pharmaceutically acceptable salt thereof together with a pharmaceutically acceptable carrier or diluent.

In a further aspect, the present invention relates to a method of binding to somatostatin receptors, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for binding to the somatostatin receptors.

Those skilled in the art will appreciate that a wide variety of prophylactic, diagnostic, and therapeutic treatments may be prepared from the synthetic compounds and compositions of the invention, due in large part to the competition—that is, agonism or antagonism—of these moieties with the naturally occurring SRIF or SRIF-28. For example, by administering an effective amount of a compound of the invention, prophylactic or therapeutic responses can be produced in a human or some other type mammal. Preferred responses are produced by modulating—that is, increasing, decreasing or otherwise modifying—the activity of at least one somatostatin receptor subtype (i.e. SSTR1, SSTR2, SSTR3, SSTR4 and SSTR5). It will be appreciated that the production of prophylactic or therapeutic responses includes the initiation or enhancement of desirable responses, as well as the cessation or suppression of undesirable responses.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, buccal, pulmonal, transdermal or parenteral, the oral route being preferred.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts ($\delta$) are given in parts per million (ppm) and only selected peaks are given. m.p. is melting point and is given in ° C. and is not corrected. Column chromatography was carried out using the technique described by W. C. Still at al, J. Org. Chem. 1978, 43, 2923–2925 on Merck silica gel 60 (Art 9385). Compounds used as starting materials are either known compounds or compounds which can readily be prepared by methods known per se.

| Abbreviations: | |
|---|---|
| TLC: | thin layer chromatography |
| DMSO: | dimethylsulfoxide |
| min: | minutes |
| h: | hours |
| HPLC-Analysis: | |
| Method A. | |

The RP-HPLC analysis was performed using UV detection at 254 nm and a Lichrosorp RP-18 5 mM column, which was eluted at 1 ml/minute. The column was equilibrated with 20% acetonitrile in a buffer consisting of 0.1M ammonium sulfate, which was adjusted to pH 2.5 with 4M sulfuric acid and eluted by a gradient of 20% to 80% acetonitrile in the same buffer over 30 minutes. The gradient was then extended to 100% acetonitrile over 5 minutes followed by isocratic elution with 100% acetonitrile for 6 minutes.

Biological assays

The affinity of somatostatin receptor ligands of nonpeptide origin according to the invention (including the compounds covered by formula I) to the somatostatin receptor proteins selected from SST1, SST2, SST3, SST4 and SST5, may be detected using the assays described below. The skilled person will know which adjustments/modifications to make in order to screen for specific ligands having affinity to one or more of the SST receptor subtypes 1–5. Moreover, in order to screen large compound libraries to find the present ligands, conventional techniques (see e.g. Amersham™ SPA Technology) known to the skilled person may be used to modify the assays. One way of producing the present ligands is to provide a compound library of nonpeptide origin using conventional techniques (see e.g. Combinatorial chemistry in the discovery and development of drugs. Doyle, P. M., Journal Of Chemical Technology And Biotechnology (1995) Vol. 64, 317–24) well-known to the skilled person, and screen for such ligands using the assays described below optionally with modifications, thereby providing somatostatin receptor ligands according to the invention.

Cell lines expressing SST receptor subtypes:

BHK cells (tk–ts13, ATCC CRL# 1632) and HEK 293 cells (ATCC CRL# 1573) were grown to 20–40% confluency in a tissue culture dish in Dulbeccos Modified Eagle Medium (DMEM) containing 1% penicillin/streptomycin, 10% foetal bovine serum, and 1% Glutamax™. Prior to transfection, the cells were washed twice with calcium-free PBS after which 20 ml of serum-free DMEM was added to the cells.

Transfection was carried out as described previously (product description: Lipofectamin, Gibco BRL cat. no. 18324-012). Briefly, 10 µg of cDNA encoding a SST receptor subtype inserted into the mammalian expression vector pcDNA3 (Invitrogen) was diluted in 300 µl of sterile water. 30 µg of Lipofectamin was diluted in 300 µl of sterile water. The cDNA and Lipofectamin solutions were mixed and left at room temperature for 15 minutes. The Lipofectamin/cDNA mixture was added drop-wise to the cells (HEK 293 cells for $SST_2$, BHK for the other receptor subtypes) while gently swirling the plates. The cells were then incubated for 16–24 hours, after which the medium was replaced with standard medium containing 1 mg/ml Geneticin (G-418 sulfate). Resistant colonies appearing after 1–2 weeks were isolated and propagated for further characterization.

Binding assay:

Cells expressing individual SST receptor subtypes were resuspended in buffer (50 mM Tris-HCl (pH 7.4), 1 mM EGTA, 5 mM $MgCl_2$), and homogenised. Membranes were washed twice in buffer by homogenisation and centrifugation. Final membrane pellets were resuspended at a protein concentration of 125 µg/ml in buffer. Binding assays using 75 pM $^{125}$I-Tyr$^{11}$-SRIF (Amersham, IM-161) were done in duplicates in minisorb polypropylene tubes in a volume of 250 µl. The assays were incubated at 30–37° C. for 30–90 min depending on receptor subtype. Binding was terminated by filtration through Whatman GF/B glass fiber filters pre-soaked for 4 hrs. in 0.5% polyethyleneimine and 0.1% BSA. Filters were washed three times with 5 ml ice-cold 0.9% saline and counted in a Packard Cobra II Gamma Counter.

Functional assay:

Cells expressing human SST receptors were seeded in 24-well tissue culture multidishes at 200,000 cells/well and grown for 16–20 hours. The medium was removed, and fresh DMEM medium, supplemented with 1) 1 mM 3-isobutyl-1-methylxanthine (IBMX), 2) 10 µM forskolin or medium, and 3) medium, SRIF, SST analogue, or compound was added. The plates were incubated for 15–30 min at 37° C., the reaction medium removed and the cells lysed with 0.1 M sodium hydroxide. Following neutralisation with 0.1 M hydrochloric acid an aliquot was removed for cAMP determination using Amersham SPA RIA (RPA 538).

Example 1

4-(1H-Imidazol-4-yl)piperidine-1-carbothioic acid (2-((5-bromopyridine-2-yl)-(3,4-dichlorobenzyl)amino)ethyl)amide

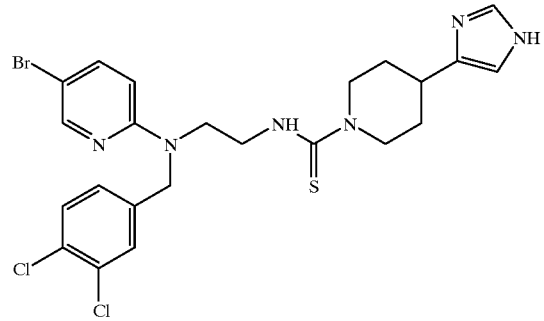

A mixture of 2,5-dibromopyridine (10.0 g, 42.2 mmol) and pyridine (4.24 g, 53.6 mmol) in 1,2-diaminoethane (43 mL) was refluxed under nitrogen for 18 h. The reaction mixture was evaporated under reduced pressure, cooled, and the resulting residue was treated with THF (150 mL) to yield a white precipitate. The precipitate was filtered and washed with additional THF (100 mL). Evaporation of the filtrate afforded a brown oil which was vacuum distilled to give 6.48 g (71%) N-1-(5-bromopyrid-2-yl)ethane-1,2-diamine as a light yellow oil.

bp 134–142° C. (0.6 mm).; $^1$H NMR (90 MHz $CDCl_3$) δ 1.33 (s, 2 H, $NH_2$), 2.92 (t, 2 H), 3.29 (m, 2 H), 5.22 (br s, 1 H, NH), 6.31 (d, J=9 Hz, 1 H, pyridine H-3), 7.44 (dd, J=2.7 Hz, 9 Hz, 1 H, pyridine H-4), 8.09 (d, J=2.5 Hz, 1 H, pyridine H-6). $^{13}$C NMR (90 MHz $CDCl_3$) δ 41.22, 44.74, 106.72, 108.67, 139.55, 148.54, 148.70.

A 60% mineral oil dispersion of sodium hydride (0.584 g, 14.6 mmol) and N-1-(5-bromopyrid-2-yl)ethane-1,2-diamine (3.00 g, 13.9 mmol) in DMSO (30 mL) was stirred for 2 h under nitrogen. The suspension was cooled to 0–5° C. and treated dropwise with 3,4-dichlorobenzyl chloride (2.71 g, 13.9 mmol) in DMSO (15 mL). After stirring overnight at room temperature, the reaction mixture was poured into 200 mL of an ice-water mixture. The mixture was extracted with ethyl acetate (3×75 mL), and the combined ethyl acetate extracts were washed with water (2×50 mL), dried ($Na_2SO_4$), filtered, and evaporated to yield an oil. Flash chromatography on silica gel using $CH_2Cl_2$ 90: $CH_3OH$ 5: $Et_3N$ 5 as the solvent system gave 3.5 g of N-1-(5-bromopyrid-2-yl)-1-(3,4-dichlorobenzyl)ethane-1,2-diamine as a yellow oil.

$^1$H NMR (90 MHz $CDCl_3$) δ 1.45 (s, 2 H, $NH_2$), 2.92 (t, 2 H, $NCH_2$), 3.57 (m, 2 H, $CH_2NH_2$), 4.72 (s, 2 H, $ArCH_2$), 6.39 (d, J=9 Hz, 1 H, pyridine H-3), 7.32 (m, 4 H, ArH), 8.16 (d, J=2 Hz, 1 H, pyridine H-6). $^{13}$C NMR (90 MHz $CDCl_3$) δ 39.82, 51.47, 51.95, 107.00, 107.27, 126.23, 128.77, 130.62, 131.04, 132.73, 138.85, 139.77, 148.66, 156.62.

A mixture of dicyclohexylcarbodiimide (DCC) (2.74 g,13.2 mmol) and carbon disulfide (10.1 g, 132.6 mmol) in THF (30 mL) was cooled to −10° C. in an ice-salt bath and treated dropwise with a solution of N-1-(5-bromopyrid-2-yl)-1-(3,4-dichlorobenzyl)ethane-1,2-diamine (5.00 g, 13.2 mmol) in THF (20 mL). The reaction mixture was allowed to warm to room temperature and was stirred overnight under nitrogen. Removal of the solvent under reduced pressure afforded a white solid. The solid was triturated with diethyl ether (200 mL), and the dicyclohexylthiourea was removed by filtration. The filtrate was evaporated, and acetonitrile (100 mL) was added to the resulting residue. The remaining dicyclohexyl thiourea was filtered, and the filtrate was evaporated under vacuum to afford an oil. Flash chromatography on silica gel using $CH_2Cl_2$ 50: hexane 50: $Et_3N$ 1 gave 4.31 g of 2-[N-(5-bromopyrid-2-yl)-N-(3,4-dichlorobenzyl)] aminoethyl isothiocyanate as a white solid. Recrystallization from diethyl ether/hexane gave an analytical sample.

mp 83–85° C. $^1H$ NMR (90 MHz $CDCl_3$) δ 3.84 (m, 4 H), 4.69 (s, 2 H, $ArCH_2$), 6.33 (d, J=8.3 Hz, 1 H, pyridine H-3), 7.40 (m, 4 H), 8.20 (d, J=2 Hz, 1 H, pyridine H-6). $^{13}C$ NMR (90 MHz $CDCl_3$) δ 43.34, 49.19, 52.71, 107.70, 108.19, 125.74, 128.34, 130.83, 140.10, 148.71, 155.65. Anal. Calcd for $C_{15}H_{12}BrCl_2N_3S$: C, 47.01; H, 3.16; N, 14.62. Found: C, 46.93; H, 3.32; N, 14.56.

A suspension of 4-(4(5)-imidazolyl)piperidine dihydrochloride (387 mg, 1.73 mmol) and triethylamine (350 mg, 3.50 mmol) in THF (30 mL) was stirred for 2 h at room temperature under nitrogen and treated dropwise with 2-[N-(5-bromopyrid-2-yl)-N-(3,4-dichlorobenzyl)] aminoethyl isothiocyanate (662 mg, 1.73 mmol) in THF (15 mL). After stirring overnight, considerable starting material remained. The reaction mixture was heated at 60° C. for 24 h, cooled to room temperature, filtered, and evaporated to yield an oil. Flash chromatography on silica gel using a solvent system of EtOAc 85: $CH_3OH$ 15: concentrated $NH_4OH$ 1 afforded 700 mg of the title compound as a white foam.

$^{13}C$ NMR ($CDCl_3$) δ 31.42, 34.78, 46.31, 47.67, 47.89, 51.46, 107.59, 108.40, 113.76, 125.79, 128.28, 130.93, 131.42, 133.05, 134.67, 137.38, 140.47, 142.09, 147.84, 157.26, 180.99. Anal. Calcd for $C_{23}H_{25}BrCl_2N_6S$: C, 48.61; H, 4.42; N, 14.79. Found: C, 49.09; H, 4.76; N, 14.54.

Example 2

1-(3H-Benzotriazol-5-yl)-3-(2-((5-bromopyridin-2-yl)-(3,4-dichlorobenzyl)amino)ethyl)thiourea

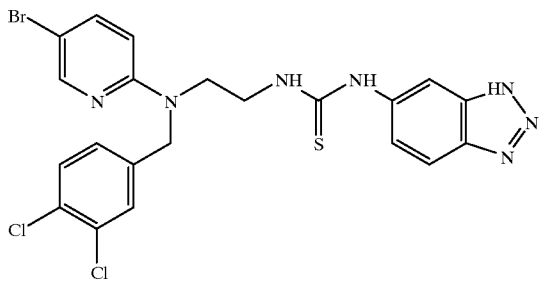

A solution of 5-aminobenzotriazole (312 mg, 2.28 mmol) in THF (40 mL) was stirred under nitrogen and treated with a solution of 2-[N-(5-bromopyrid-2-yl)-N-(3,4-dichlorobenzyl)] aminoethyl isothiocyanate (950 mg, 2.28 mmol) in THF (25 mL). After stirring overnight, a TLC (silica gel, EtOAc 9: $CH_3OH$ 1: concentrated $NH_4OH$ 0.5) of the reaction mixture indicated that only starting material was present. The reaction mixture was refluxed for 48 h, cooled to room temperature, and evaporated under reduced pressure to afford a brown foam. Trituration of the foam with hexane afforded a solid which was recrystallized from ethyl acetate-hexane to give 1.08 g of the title compound: mp 189.5–191.5° C.; $^1H$ NMR (DMSO-$d_6$) δ 3.67 (m, 4 H), 4.78 (s, 2 H, $ArCH_2$), 6.78–8.06 (m, 11 H), 9.86 (s, 1 H, N=N—NH); $^{13}C$ NMR (DMSO-$d_6$) δ 46.84, 50.01, 106.02, 108.08, 115.99, 122.92, 127.04, 128.67, 129.21, 130.56, 131.00, 136.47, 139.94, 147.63, 156.24, 180.72. Anal. Calcd for $C_{21}H_{19}BrCl_2N_7S$: C, 45.67; H, 3.47; N, 17.75. Found: C, 45.94; H, 3.40; N, 17.87.

Example 3

1-(2-((5-Bromopyridin-2-yl)-(3,4-dichlorobenzyl)amino)ethyl)-3-(4-piperidine-1-ylphenyl)thiourea

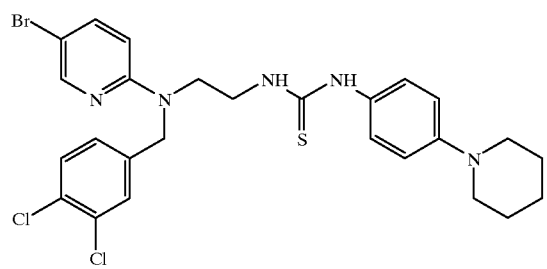

A solution of N-(4-aminophenyl)piperidine (388 mg, 2.16 mmol) in THF (40 mL) was stirred under nitrogen and treated dropwise with 2-[N-(5-bromopyrid-2-yl)-N-(3,4-dichlorobenzyl)] aminoethyl isothiocyanate (0.90 g, 2.16 mmol) in THF (15 mL). The reaction mixture was stirred at 40° C. for an additional 24 h. Evaporation of the solvent afforded a dark brown oil. Trituration with hexane gave a solid which was recrystallized from diethyl ether-hexane to yield 930 mg of a the title compound: mp 146–147.5° C.; $^1H$ NMR ($CDCl_3$) d 1.66 (m, 6 H), 3.21 (m, 4 H), 3.80 (br s, 4 H), 4.85 (s, 2 H, ArCH2), 6.32 (d, 1 H, pyridine H-3), 7.30 (m, 11 H, ArH and NHC=SNH); $^{13}C$ NMR ($CDCl_3$) d 24.16, 25.67, 45.07, 47.07, 49.84, 51.30, 107.59, 116.52, 125.73, 127.36, 128.23, 130.83, 137.60, 140.04, 148.11, 151.36, 156.56, 181.37. Anal. Calcd for $C_{26}H_{28}BrCl_2N_5S$: C, 52.62; H, 4.76; N, 11.80. Found: C, 52.61; H, 4.69; N, 11.78.

Example 4

1-(2-((5-Bromopyridin-2-yl)-(3,4-dichlorobenzyl)amino)propyl)-3-(4-piperidine-1-ylphenyl)thiourea

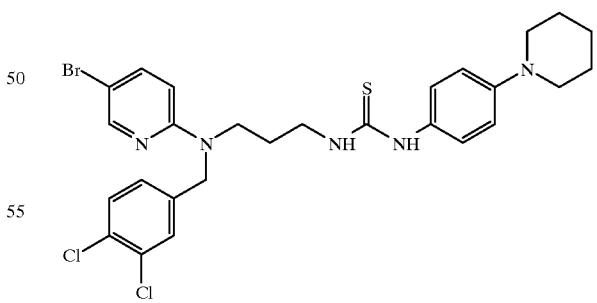

The title compound was prepared analogously to example 3 with 2-[N-(5-bromopyrid-2-yl)-N-(3,4-dichlorobenzyl)] aminopropyl isothiocyanate instead of with 2-[N-(5-bromopyrid-2-yl)-N-(3,4-dichlorobenzyl)]aminoethyl isothiocyanate. mp 125–127° C.; 1H NMR ($CDCl_3$) δ 1.69 (m, 8 H), 3.22 (m, 4 H), 3.63 (m, 4 H), 4.49 (s, 2 H, ArCH2), 6.15 (d, 9 Hz, 1 H, pyridine H-3), 6.90–7.56 (m, 11 H). Anal.

Calcd. For $C_{27}H_{30}BrCl_2N_5S$: C, 53.39; H, 4.98; N, 11.53. Found: C,53.29; H, 4.99; N, 11.16.

Example 5

1-(2-((5-Bromopyridin-2-yl)-(3,4-dichlorobenzyl) amino)butyl)-3-(3-(1H-imidazol-4-yl)phenyl) thiourea

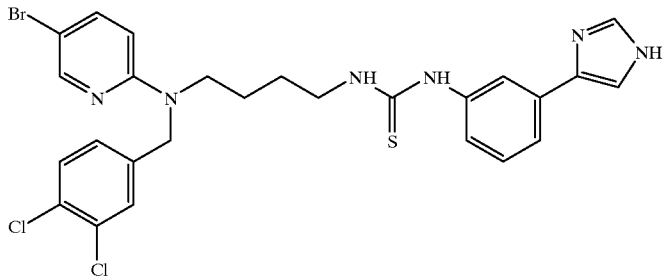

The title compound was prepared analogously to example 3 with 2-[N-(5-bromopyrid-2-yl)-N-(3,4-dichlorobenzyl)] aminobutyl isothiocyanate instead of with 2-[N-(5-bromopyrid-2-yl)-N-(3,4-dichlorobenzyl)]aminoethyl isothiocyanate and 4-(3-aminophenyl)-1H-imidazole instead of N-(4-aminophenyl)piperidine. mp 140–160° C.; $^1$H NMR (CDCl$_3$) δ 1.49 (m, 4 H), 3.47 (m, 4 H), 4.51 (s, 2 H, ArCH2), 6.22 (d, 1 H, pyridine H-3), 7.30 (m, 10 H), 8.00 (d, 1 H, pyridine H-6), 8.53 (br s, 1 H, imidazole N—H); $^{13}$C NMR (CDCl$_3$) δ 24.43, 26.38, 44.85, 48.48, 50.92, 106.67, 107.32, 121.51, 123.41, 126.17, 126.61, 128.61, 130.18, 130.56, 130.88, 132.56, 135.11, 135.97, 137.11, 138.79, 148.43, 156.18, 180.56.

Example 6

N1-[3-[N-(4-Bromo-benzyl)-N-(pyridin-2-yl)amino] propyl]-4-(pyridin-2-yl)piperazine-1-carboxamidine trihydrochloride

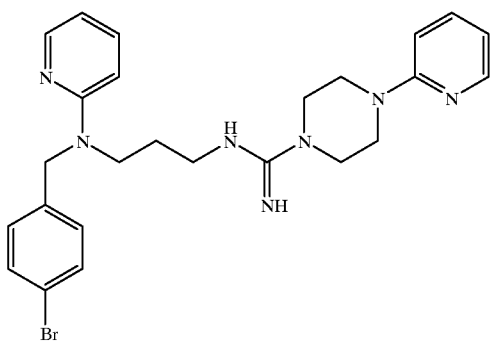

To a solution of propane-1,3-diamine (310 ml, 3.63 mol) in dry pyridine (75 ml) kept under an atmosphere of nitrogen 2-bromo-pyridine (70 ml, 0.73 mol) was added. The reaction mixture was heated at reflux for 18 h, cooled and the volatiles evaporated in vacuo. To the residue was added tetrahydrofuran (1000 ml) and the precipitate was filtered off and washed with tetrahydrofuran (500 ml). The solvent was evaporated in vacuo and the residue purified by distillation at 95–97° C. and 2·10$^{-2}$ mbar affording 83.37 g of N1-(pyridin-2-yl)propyl-1,3-diamine.

$^1$H NMR (200 MHz, DMSO-d$_6$) δ$_H$ 1.20 (bs, 2H, NH$_2$), 1.74 (p, 2H), 2.82 (t, 2H), 3.34 (q, 2H, CH$_2$—NH), 4.86 (bs, 1H, NH), 6.35 (dt, 1H), 6.51 (ddd, 1H), 7.37 (ddd, 1H), 8.04 (ddd, 1H).

To a mixture of sodium hydride (5.86 g, 60% dispersion in mineral oil, 0.1415 mol) in dry dimethylsulfoxide (250 ml) was slowly added a solution of N1-(pyridin-2-yl) propane-1,3-diamine (20 g, 0.1323 mol) in dry dimethyl-sulfoxide (50 ml) at room temperature under an atmosphere of nitrogen. The reaction mixture was stirred until gas evolution had exceed. A solution of 4-bromobenzyl bromide (36.09 g, 0.1415 mol) in dry dimethylsulfoxide (100 ml) was slowly added at room temperature. The reaction mixture was stirred for 48 h at room temperature. The reaction mixture was poured onto ice water (500 ml) and extracted with ethyl acetate (3×250 ml). The combined organic extracts were washed with water (3×150 ml), dried (MgSO4), filtered and concentrated in vacuo. The residue (40.56 g) was washed with n-heptane (30 ml) which afforded 36.77 g of crude N-1-(4-bromobenzyl)-N-1-(pyridin-2-yl)propane-1,3-diamine. The crude product (20 g) was purified by column chromatography on silica gel (900 ml) using dichloromethane/methanol/triethylamine 9:0.5:0.5 as eluent affording 13.75 g of N1-(4-bromobenzyl)-N1-(pyridin-2-yl)-propane-1,3-diamine as an oil.

$^1$H NMR (200 MHz, CDCl$_3$) δ $_H$ 1.64 (s, 2H, NH$_2$), 1.74 (t, 2H), 2.72 (t, 2H), 3.60 (t, 2H, CH$_2$—N), 4.67 (s, 2H, CH$_2$—Ph), 6.41 (d, 1H), 6.53 (dd, 1H), 7.07 (d, 2H), 7.33–7.41 (m, 3H), 8.13 (dt, 1H).

To a mixture of 1-(2-pyridyl)piperazine (10 ml, 64.37 mmol) in dichloromethane (200 ml) was added N-benzoyldimethyldithioimidocarbonate (14.64 g, 65.01 mmol) and the reaction mixture was stirred for 18 h at room temperature. The volatiles were evaporated in vacuo and the residue crystallised from a mixture of heptane/diethyl ether 9:1. The solid was filtered off, washed with a mixture of heptane/diethyl ether 1:1 and dried in vacuo affording 20.86 g of N-[methylsulfanyl-(4-(pyridin-2-yl)piperazin-1-yl) methylene]-benzamide as a solid.

To a mixture of N-[methylsulfanyl-(4-(pyridin-2-yl) piperazin-1-yl)methylene]-benzamide (2.9 g, 8.52 mmol) in pyridine (50 ml) was added N1-(4-bromobenzyl)-N1-(pyridin-2-yl)-propane-1,3-diamine (3 g, 9.37 mmol) and the reaction mixture was heated at reflux for 18 h. The volatiles were evaporated in vacuo and the residue dissolved in dichloromethane (100 ml) and evaporated in vacuo. The residue was purified by column chromatography on silica gel (600 ml) using first a mixture of ethyl acetate/ triethylamine 95:5 (1 l) followed by a mixture of 20 ethyl acetate/methanol/triethylamine 90:5:5 as eluents affording 2.95 g of N-[[3-[N-(4-bromo-benzyl)-N-(pyridin-2-yl) amino]propylamino]-(4-pyridin-2-yl-piperazin-1-yl) methylene]benzamide as a foam.

N-[[3-[N-(4-bromo-benzyl)-N-(pyridin-2-yl)amino]propylamino]-(4-(pyridin-2-yl)piperazin-1-yl) methylene]benzamide(0.5 g, 0.816 mmol) was dissolved in 1.5 N hydrochloric acid (10 ml) and heated at 100° C. for 21 h in a screw cap ampoule. The cooled reaction mixture was washed with diethyl ether (3×10 ml) and evaporated in vacuo affording a residue which was dissolved in ethanol (20 ml) and evaporated in vacuo the later repeated three times affording 496 mg of crude product as a foam. The crude product (496 mg) was suspended in 30% sodium methoxide in methanol (0.51 ml) and stirred at room temperature for 10 min. To the reaction mixture was added a solution of di-tert-butyl dicarbonate (361 mg, 1.61 mmol) in dioxane (25 ml) and the resulting mixture was stirred for 18 h at room temperature. The reaction mixture was filtered and the volatiles were evaporated in vacuo affording 611 mg of a syrup which was purified by column chromatography on silica gel (180 ml) using first a mixture of ethyl acetate/methanol 90:10 as eluent affording 215 mg of [[3-[N-(4-Bromobenzyl)-N-(pyridin-2-yl)amino]propylamino]-(4-(pyridin-2-yl)piperazin-1-yl)methylene]carbamic acid tert-butyl ester as foam. To a mixture of the tert-butyl ester (215 mg, 0.353 mmol) in ethyl acetate (15 ml) was added 1N hydrochloric acid in diethyl ether (1.8 ml, 1.77 mmol) and the reaction mixture was stirred for 61 h at room temperature. The reaction mixture was evaporated in vacuo and to the residue dissolved in methanol (10 ml) was added 1N hydrochloric acid in diethyl ether (22 ml, 1.77 mmol). The resulting mixture was stirred for 60 h at room temperature. The reaction mixture was evaporated in vacuo and the residue was dissolved in ethanol (15 ml) and evaporated in vacuo affording 194 mg of the title compound as a foam.

$^1$H NMR (400 MHz, D$_3$COD) $\delta_H$ 2.12 (m, 2H), 3.46 (t, 2H), 3.84 (m, 6H), 3.93 (m, 4H), 4.96 (s, 2H, CH$_2$—Ph), 7.05 (m, 2H), 7.26 (m, 3H), 7.39 (d, 1H), 7.55 (d, 2H), 8.00–8.12 (m, 4H).

What is claimed is:

1. A compound formula I

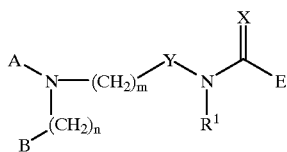

(I)

wherein

A is pyridinyl or phenyl optionally substituted with one or more halogens, amino groups, hydroxyl groups, nitro groups, C$_{1-6}$-alkyl groups or C$_{1-6}$-alkoxy groups;

B is phenyl, pyridinyl or naphthyl optionally substituted with one or more halogens, amino groups, hydroxyl groups, C$_{1-6}$-alkyl groups or C$_{1-6}$-alkoxy groups;

m is 0, 1, 2, 3, 4, 5 or 6;

n is 0, 1, 2 or 3;

Y is a valence bond or a group having the formula

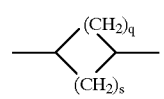

wherein q and s each independently are 0, 1, 2, 3, 4 or 5 and q+s is 1, 2, 3, 4 or 5;

R$^1$ is hydrogen or C$_{1-6}$-alkyl optionally substituted with halogen, amino, hydroxy or alkoxy;

X is =S, =O or =NR$^3$, wherein R$^3$ is hydrogen, —C(O)Ph, or —CN;

E is a group having the formula

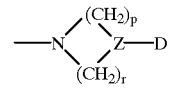

wherein p is 0, 1, 2, 3 or 4, r is 1, 2, 3, 4, 5 or 6, Z is —N< or —CH<, D is aryl optionally substituted with one or more halogens, amino groups, hydroxyl groups, C$_{1-6}$-alkyl groups, C$_{1-6}$-alkoxy groups, piperidinyl groups or aryl groups, R$^2$ is hydrogen or C$_{1-6}$-alkyl optionally substituted with halogen, amino, hydroxy, alkoxy or aryl, with the proviso that if m=0 then Y is not a valence bond; or a pharmaceutically acceptable salt thereof.

2. The compound of claim 1 wherein A is pyridinyl.

3. The compound of claim 1 wherein B is phenyl.

4. The compound of claim 1 wherein B is naphthyl.

5. The compound of claim 1 wherein D is phenyl, benzotriazolyl, imidazolyl or pyridinyl, optionally substituted with one or two halogens, amino groups, hydroxyl groups, C$_{1-6}$-alkyl groups, C$_{1-6}$-alkoxy groups, piperidinyl groups or aryl groups.

6. The compound of claim 1 wherein D is phenyl substituted with an imidazolyl group or is imidazolyl, optionally substituted with one or two halogens, amino groups, hydroxyl groups, C$_{1-6}$-alkyl groups, C$_{1-6}$-alkoxy groups, piperidinyl groups or aryl groups.

7. The compound of claim 1 wherein D is 1H-imidazol-4-yl.

8. The compound of claim 1 wherein D is pyridin-2-yl.

9. The compound of claim 1 which is:

4-(1H-Imidazol-4-yl)piperidine-1-carbothioic acid (2-((5-bromopyridin-2-yl)-(3,4-dichlorobenzyl)amino)ethyl) amide;

N$^1$-(3-(N-(4-Bromobenzyl)-N-(pyridin-2-yl)amino)propyl)-4-(pyridin-2-yl)piperazine-1-carboxamidine;

N$^1$-(3-(N-(4-Bromobenzyl)-N-(pyridin-2-yl)amino)cyclopentyl)-4-(pyridin-2-yl)piperazine-1-carboxamidine;

or a pharmaceutically acceptable salt thereof.

10. A pharmaceutical composition comprising a compound of claim 1 together with a pharmaceutically acceptable carrier or diluent.

11. A method for treatment of type I diabetes, type II diabetes, CFS, endocrine tumors, exocrine tumors, dwarfism, acromegaly, other growth abnormalities, autoimmune diseases, rheumatoid arthritis, Alzheimer's disease, pain, anxiety, memory disorders, affective disorders, intestinal water congestion, diarrhea, restenosis, arteriosclerosis, asthma, mucoviscidosis, obesity, ulcer, acute pancreatitis, a disease associated with an adverse condition in the retina and/or iris-ciliary body, comprising administering to a subject in need thereof an effective amount of a compound of claim 1.

* * * * *